(12) United States Patent
Rüffert

(10) Patent No.: US 7,833,166 B2
(45) Date of Patent: Nov. 16, 2010

(54) BREATH ALCOHOL-MEASURING DEVICE WITH AN ILLUMINATED MOUTHPIECE

(75) Inventor: Lutz Rüffert, Scharbeutz (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 11/877,869

(22) Filed: Oct. 24, 2007

(65) Prior Publication Data
US 2008/0171947 A1    Jul. 17, 2008

(30) Foreign Application Priority Data
Jan. 17, 2007    (DE) .................. 10 2007 002 505

(51) Int. Cl.
*A61B 5/06* (2006.01)
(52) U.S. Cl. .................. 600/532; 600/529; 73/23.3
(58) Field of Classification Search .......... 600/532, 600/529, 538; 180/272; 422/84, 85; 73/23.3; 702/22, 24
See application file for complete search history.

(56) References Cited

U.S. PATENT DOCUMENTS

| 4,617,821 | A |   | 10/1986 | Yokoyama et al. |         |
|-----------|---|---|---------|-----------------|---------|
| 4,656,008 | A |   | 4/1987  | Gump            |         |
| 4,768,520 | A | * | 9/1988  | Varraux et al.  | 600/538 |
| 4,916,435 | A |   | 4/1990  | Fuller          |         |
| 5,291,898 | A | * | 3/1994  | Wolf            | 600/532 |
| 2001/0019479 | A1 | * | 9/2001  | Nakabayashi et al. | 362/31 |
| 2001/0056222 | A1 | * | 12/2001 | Rudischhauser et al. | 600/130 |
| 2002/0029003 | A1 | * | 3/2002  | Mace et al.     | 600/532 |
| 2004/0204655 | A1 | * | 10/2004 | Stock et al.    | 600/532 |
| 2004/0260194 | A1 | * | 12/2004 | Bayer et al.    | 600/529 |
| 2006/0217625 | A1 |   | 9/2006  | Forrester       |         |
| 2007/0016092 | A1 | * | 1/2007  | Shaw et al.     | 600/532 |

FOREIGN PATENT DOCUMENTS

| DE | 103 16 333 B3 | 1/2004 |
| GB | 2 400 321     | 10/2004 |
| JP | 6 215 7572    | 7/1987 |
| KR | 20060099689   | 9/2006 |

OTHER PUBLICATIONS

Alco-sensor FST, Intoximeters Inc., www.intox.com, printed Apr. 2005; obtained from http://www.padui.org/lawenforce/lawstore/AS%20FST_APRIL_2005.pdf; Alcohol Sensor.

* cited by examiner

*Primary Examiner*—Charles A Marmor, II
*Assistant Examiner*—Christian Jang
(74) *Attorney, Agent, or Firm*—McGlew and Tuttle, P.C.

(57) ABSTRACT

A breath alcohol-measuring device is provided, which includes a mouthpiece which can be inserted or attached, with a blow-in opening and with a blow-out opening and with a hole for breathing gas sampling in the breath alcohol-measuring device. The breath alcohol-measuring device (2) is equipped with a radiation source (3) and with a light guide (4) receiving the radiation of the radiation source (3). The light guide (4) is arranged extending from the housing of the breath alcohol-measuring device (2) up to the blow-out opening of the mouthpiece (1) such that the light guide (4) acts as an illuminating means for the mouthpiece (1).

20 Claims, 1 Drawing Sheet

BREATH ALCOHOL-MEASURING DEVICE WITH AN ILLUMINATED MOUTHPIECE

CROSS REFERENCE TO RELATED APPLICATIONS

This application claims the benefit of priority under 35 U.S.C. §119 of German Patent Application DE 10 2007 002 505.1 filed Jan. 17, 2007, the entire contents of which are incorporated herein by reference.

FIELD OF THE INVENTION

The present invention pertains to a breath alcohol-measuring device with an illuminated mouthpiece.

BACKGROUND OF THE INVENTION

Breath alcohol-measuring devices have a generally replaceable tubular mouthpiece, into which the test person releases a breath sample. A breath sample is taken by the breath alcohol-measuring device by means of a pumping or suction means from the breath flow flowing through the mouthpiece, in general, via a hole in the mouthpiece, and this breath sample is analyzed in the measuring device especially by means of electrochemical or infrared optical alcohol sensors or optionally also by means of alcohol sensors on the basis of semiconductor elements with respect to the measurable breath alcohol concentration.

The general design of such a breath alcohol-measuring device with a replaceable mouthpiece is described, for example, in DE 103 16 333 B3.

SUMMARY OF THE INVENTION

The object of the present invention is to perfect the breath alcohol-measuring device, which is known per se, in terms of improved handling for the performance of the breath alcohol sampling of a test person even under poor visibility conditions.

According to the invention, a breath alcohol-measuring device is provided with a mouthpiece which can be inserted or attached. The mouthpiece has a blow-in opening and has a blow-out opening and with a hole for a breathing gas sampling for an alcohol sensor. The breath alcohol-measuring device is equipped with a radiation source and with a light guide receiving the radiation of the radiation source. The light guide is arranged extending from the housing of the breath alcohol-measuring device up to the blow-out opening of the mouthpiece such that the light guide is used as an illuminating means for the mouthpiece.

The essential advantage of the present invention is that the handling of the breath alcohol-measuring device for the operator is markedly improved in terms of the positioning and attaching of the mouthpiece with components that are known per se.

The sampling is facilitated for the test person by the good recognizability of the mouthpiece.

The light guide may act as a stop for positioning the mouthpiece, which can be inserted or attached.

The radiation source may advantageously be an LED and the light guide may be a glass fiber element. The light guide may be an injection-molded element.

The radiation source may emit radiation in different color ranges. The different color ranges may correspond to different operating or functional states of the breath alcohol-measuring device.

The alcohol sensor may advantageously be an electrochemical sensor. The radiation source and the light guide may be designed as an optical component in one assembly unit.

An exemplary embodiment of the subject of the present invention will be explained below on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
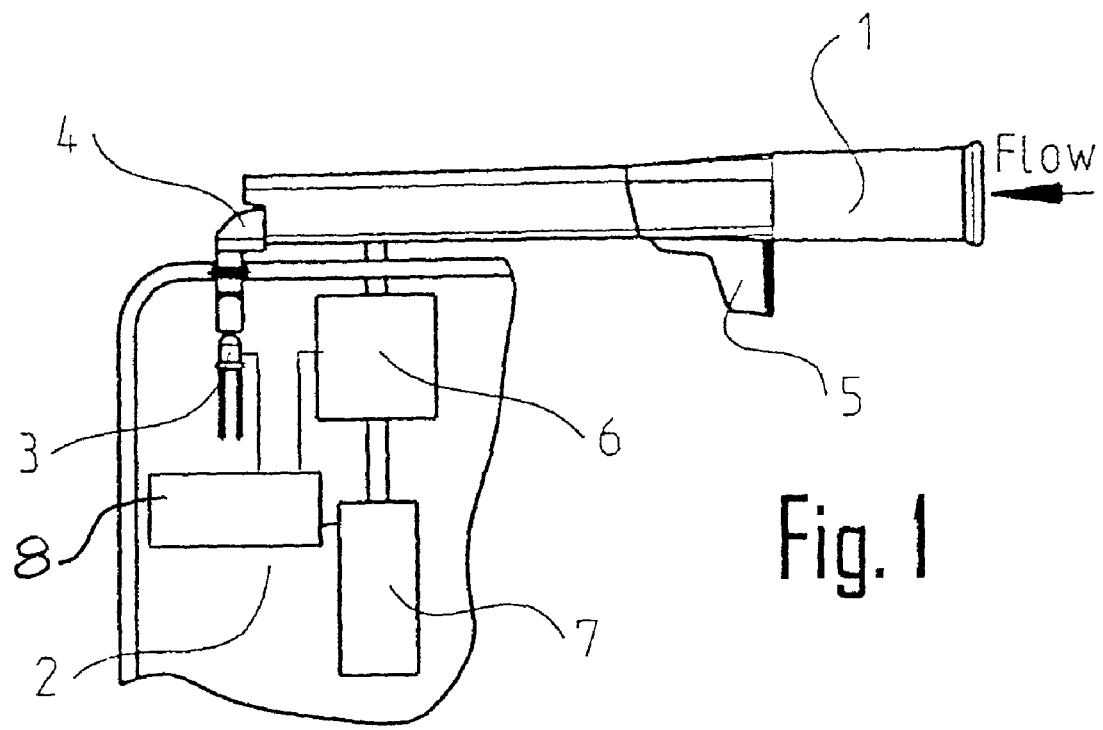
FIG. 1 is a schematic sectional view in the longitudinal direction through a breath alcohol-measuring device with an attachable mouthpiece on the right-hand side.
Figure 2:
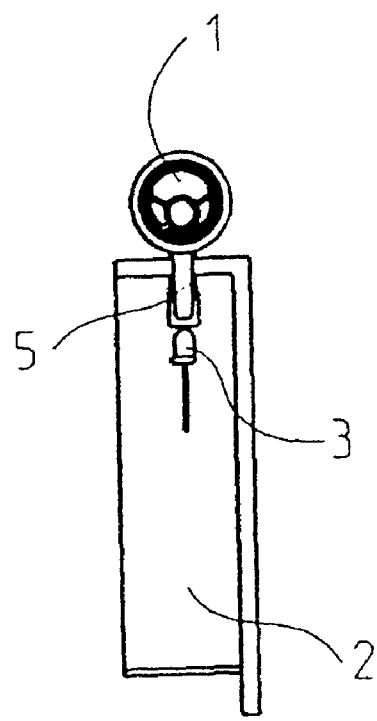
FIG. 2 is a schematic sectional view of the breath alcohol-measuring device with an attachable mouthpiece with the view being at right angles to the section of FIG. 1 looking into the mouthpiece and showing a cut just forward (just to the right in FIG. 1) of the LED, with the small ring in the mouthpiece being a light guide.

Referring to the drawings in particular, the mouthpiece 1 is made in the form of a hollow cylinder from an at least partially transparent plastic as the wall material.

A breathing gas sampling is started by the breath alcohol-measuring device 2 as a function of the breath flow (flow) detected via a hole in the mouthpiece 1, which hole is connected to a pump 7 by means of a flow line via an alcohol sensor 6.

The mouthpiece 1 has a blow-in opening on the right, which is characterized by the arrow pointing to the left with the label "FLOW" corresponding to the direction of the breath flow released by a test person. The blow-out opening of the mouthpiece 1 is located on the left.

The additional grip element 5 optionally present at the mouthpiece 1 is used additionally for the correct orientation for receiving the mouthpiece 1 in the housing of the breath alcohol-measuring device 2.

A light-emitting radiation source 3, for example, a light-emitting diode (LED), which, in this embodiment, guides the light radiated in by means of a light guide 4, for example, glass fiber element, from the housing of the breath alcohol-measuring device 2 into the blow-out-side opening of the attached or plugged-in mouthpiece 1, is located in the housing of the breath alcohol-measuring device 2.

The light guide 4 is also used at the same time as a stop for the correct positioning of the mouthpiece 1 in or on the alcohol-measuring device 2. The light emitted by the light guide 4 is radiated diffusely into the environment through the mouthpiece 1, which is thus illuminated from the inside and consists of a plastic which is transparent to light (or translucent), so that handling is substantially improved for both the operator of the mouthpiece 2 and the test person in terms of recognizability and handling.

The radiation source 3 and the light guide 4 may also be embodied in one assembly unit as an optical element.

Depending on the desired use, the illumination is present permanently after the breath alcohol-measuring device 2 has been switched on or it is activated temporarily by a separate actuation of a switch element.

The radiation source 3 emits radiation in different color ranges. Different operating states of the breath alcohol-measuring device 2, for example, for the sampling phase, an analysis phase or readiness for measurement, can be displayed by varying the color of the light emitted by the radiation source 3. A control unit 8 is connected to the pump 7 and the alcohol sensor 6. The electronic control unit 8 is also connected to the radiation source 3 and controls the radiation source to emit predetermined colors of the different color ranges based on current different operating or functional states of the breath alcohol-measuring device The power supply and the switching of the radiation source 3 is connected to the electronic control unit 8 of the breath alcohol-measuring device 2.

While a specific embodiment of the invention has been shown and described in detail to illustrate the application of the principles of the invention, it will be understood that the invention may be embodied otherwise without departing from such principles.

What is claimed is:

1. A breath alcohol-measuring device comprising:
a breath alcohol-measuring device housing;
an alcohol sensor connected to said housing;
a mouthpiece with a blow-in opening and with a blow-out opening and with a sample hole for a breathing gas sampling for said alcohol sensor, said mouthpiece being detachably connected to said housing;
a radiation source; and
a light guide receiving radiation of said radiation source, said light guide being arranged extending from said breath alcohol-measuring device housing up to said blow-out opening of said mouthpiece such that said light guide provides an illuminating means for illuminating an interior of said mouthpiece.

2. A breath alcohol-measuring device in accordance with claim 1, wherein said light guide forms a stop for positioning said mouthpiece, said mouthpiece being detachably connected to said housing which can be inserted or attached.

3. A breath alcohol-measuring device in accordance with claim 1, wherein said radiation source is a light emitting diode (LED) and said light guide is a glass fiber element.

4. A breath alcohol-measuring device in accordance with claim 1, wherein said light guide is an injection-molded element.

5. A breath alcohol-measuring device in accordance with claim 1, wherein:
said mouthpiece is at least partially transparent to light or translucent; and
said radiation source emits radiation in different color ranges illuminating the interior of the mouthpiece in any selected one of the color ranges and for being viewed from an exterior of the mouthpiece.

6. A breath alcohol-measuring device in accordance with claim 5, further comprising a control unit, wherein the different color ranges correspond to different operating or functional states of said breath alcohol-measuring device, said control unit controlling said radiation source to emit predetermined colors of said different color ranges based on a current different operating or functional state of the breath alcohol-measuring device.

7. A breath alcohol-measuring device in accordance with claim 1, wherein said alcohol sensor is an electrochemical sensor.

8. A breath alcohol-measuring device in accordance with claim 1, wherein said radiation source and said light guide are designed as an optical component in one assembly unit.

9. A breath alcohol-measuring device comprising:
a breath alcohol-measuring device housing;
an alcohol sensor connected to said housing;
an at least partially transparent to light or translucent mouthpiece detachably mounted on said housing, said mouthpiece having a blow-in opening, a blow-out opening and a sample hole with an operative connection to said alcohol sensor for providing a breathing gas sampling for said alcohol sensor;
a light source; and
a light guide receiving radiation of said light source, said light guide being arranged extending from said breath alcohol-measuring device housing up to an operative connection with said mouthpiece blow-out opening for directing light into said mouthpiece with said light guide guiding light into the mouthpiece to illuminate an interior of said mouthpiece, with said light being visible from an exterior of said mouthpiece.

10. A breath alcohol-measuring device in accordance with claim 9, wherein said light guide forms a stop for positioning said mouthpiece.

11. A breath alcohol-measuring device in accordance with claim 9, wherein said light source comprises a light emitting diode and said light guide is a fiber optic element.

12. A breath alcohol-measuring device in accordance with claim 9, wherein said light guide is an injection-molded element.

13. A breath alcohol-measuring device in accordance with claim 9, wherein said light source emits radiation in different color ranges.

14. A breath alcohol-measuring device in accordance with claim 13, further comprising a control unit, wherein the different color ranges correspond to different operating or functional states of said breath alcohol-measuring device, said control unit controlling said light source to emit predetermined colors of said different color ranges based on a current different operating or functional state of the breath alcohol-measuring device.

15. A breath alcohol-measuring device in accordance with claim 9, wherein said alcohol sensor is an electrochemical sensor.

16. A breath alcohol-measuring device in accordance with claim 9, wherein said light source and said light guide are designed as an optical component in one assembly unit.

17. A process for breath alcohol-measuring, the process comprising the steps of:
providing a breath alcohol-measuring device housing;
providing an alcohol sensor connected to said housing;
detachably mounting an at least partially transparent to light or translucent mouthpiece on said housing, said mouthpiece having a blow-in opening, a blow-out opening and a sample hole with an operative connection to said alcohol sensor for providing a breathing gas sampling for said alcohol sensor;
providing a light source;
providing a light guide for receiving radiation of said light source, said light guide being arranged extending from said breath alcohol-measuring device housing to said blow-out opening of said mouthpiece;
illuminating an interior of said mouthpiece with said light source via said light guide;
operating said alcohol sensor with said mouthpiece and said housing connected as a breath alcohol-measuring device and with light illuminating the interior of said mouthpiece visible from an exterior of said mouthpiece; and
measuring breath alcohol of a subject via the mouthpiece.

18. A process in accordance with claim 17, wherein:
said light guide forms a stop for positioning said mouthpiece;
said light source comprises a light emitting diode; and
said light guide is a fiber optic element.

19. A process in accordance with claim 17, wherein said light guide is formed by injection-molding.

20. A process in accordance with claim 17, further comprising providing a control unit, wherein said light source emits radiation in different color ranges and wherein the different color ranges correspond to different operating or functional states of the breath alcohol-measuring device, said control unit controlling said light source to emit predetermined colors of said different color ranges based on a current different operating or functional state of the breath alcohol-measuring device.

* * * * *